US005120543A

United States Patent [19]

Hagin et al.

[11] Patent Number: 5,120,543

[45] Date of Patent: Jun. 9, 1992

[54] MOLLUSCICIDAL β-CARBOLINE CARBOXYLIC ACIDS AND METHODS USING THE SAME

[75] Inventors: Roger D. Hagin, Freeville; Suzanne J. Bobnick, Genoa, both of N.Y.

[73] Assignee: The United States of America as represented by the Secretary of Agriculture, Washington, D.C.

[21] Appl. No.: 726,731

[22] Filed: Jul. 2, 1991

Related U.S. Application Data

[63] Continuation of Ser. No. 454,491, Dec. 21, 1989, abandoned.

[51] Int. Cl.[5] .......... A01N 25/08

[52] U.S. Cl. .......... 424/410; 424/84; 424/405; 424/408; 546/85

[58] Field of Search .......... 424/410, 405, 408, 84; 546/85

[56] References Cited

U.S. PATENT DOCUMENTS 4,894,457 1/1990 Kubo .......... 546/85

OTHER PUBLICATIONS

Hagin, R. D., Agric. Food Chem., vol. 37, No. 4, (1989), pp. 1143-1149.

*Primary Examiner*—Thurman K. Page
*Assistant Examiner*—D. Gabrielle Phelan
*Attorney, Agent, or Firm*—M. Howard Silverstein; Randall E. Deck; John D. Fado

[57] ABSTRACT

Slug populations can be controlled in minimum or no-tillage methods of crop production using β-carboline carboxylic acids. These compounds and their analogs can be formulated into slug bait compositions for use in erradication of these crop pests. The compositions are extremely effective at luring slugs from crop plants to the bait as well as killing them.

6 Claims, No Drawings

MOLLUSCICIDAL β-CARBOLINE CARBOXYLIC ACIDS AND METHODS USING THE SAME

BACKGROUND OF THE INVENTION

This application is a continuation of application Ser. No. 07/454,491, filed Dec. 12, 1989, now abandoned.

FIELD OF THE INVENTION

This invention relates to the use of β-carboline carboxylic acids, more specifically, 6-hydroxy-1,2,3,4-tetrahydro-βcarboline -3-carboxylic acid and its analogs, as molluscicides. These compounds effectively control slug population in minimum or no-tillage methods of crop production.

DESCRIPTION OF THE PRIOR ART

Minimum or no-tillage methods of crop production have gained increasing acceptance since the early 1950's. These methods improve timeliness of operations and reduce soil erosion which are both important objectives in the farming industry. No-tillage methods, in which weed cover is killed by chemicals and the crop planted directly thereafter, represent desirable means to achieve these objectives. Problems related to perennial weeds, insects, pathogens, slugs and snails, and possible allelopathic compounds released from killed weeds, remain as impediments to fuller utilization of no-tillage procedures. These problems are particularly severe in the temperate, humid, northeastern region of the United States. All, et al., "No-Tillage and Surface-Tillage Agriculture," Sprague, et al. (eds.), John Wiley & Sons, New York, 1986, pp. 367-368, considered that the most serious minimum tillage problem was related to attacks by slugs on crop seed and seedlings, particularly on killed sods that had not been tilled for a number of years. In New York: Ramsey, "A Comparison of Biological, Physical and Organic Matter Characteristics in No-Till and Conventional Till Continuous Corn (Zea mays)," Master's Thesis, Cornell University, August 1984, reported that slugs were a major problem in continuous no-till corn (Zea mays); Dowling, et al., Crop Protection, vol. 4, no. 3, (1985), pp. 394-402, reported that slugs were a primary limitation to the establishment of sod seeded lucerne (alfalfa, *Medicago sativa* L.).

A relatively large number of chemicals are available to deal with weeds, insects, plant pathogens and other pests. However, only two are available for control of slugs and snails at this time and they are metaldehyde and methiocarb. Of the two, methiocarb is the more effective in humid regions. Both compounds suffer the disadvantages of being relatively expensive and toxic to mammals and/or birds. Metaldehyde, currently the most widely used molluscicide for slugs has been reported frequently as the cause of poisoning of dogs, cats, sheep and poultry [Homeida, et al., J. Vet. Pharmacol. Therap., vol. 5, (1982), pp. 77-81 and Osweiler, et al., "Clinical and Diagnostic Veterinary Toxicology," Kendal/Hunt, Dubuque, Iowa, 3rd ed., 1985, pp. 3-8].

In the state of Delaware, according to press reports, the most effective treatment available for slugs in no-till corn was liquid nitrogen fertilizer applied to early stage corn at night after slugs had emerged onto crop plants ["Search Out Slugs Now in No-Till Fields," Lancaster Farming, vol. 34, no. 20, (1989), p. C-2].

The fertilizer presumably kills slugs by salt effects, causing them to emit copious amounts of slime followed by desiccation of the animals. The method is limited by the requirement to spray the material directly on the slugs. Clearly, there is a need for additional molluscicides that are highly selective and toxic for slugs and/or snails with minimal effect on other species.

Exploratory work by Hagin, et al., Abstract of Papers, National Meeting of the Weed Science Society of America, Sheraton Inn, Seattle, WA, Feb. 5-7, 1985, Abstract 170, indicated that phenolic glucoside fractions from extracts of dried quackgrass roots were both dermally and gastrointestinally toxic to the slugs *Deroceras reticulatum* and *Deroceras laeve*. The exact compound or compounds were not identified.

SUMMARY OF THE INVENTION

This invention provides methods of controlling slugs that do not suffer the disadvantages of prior art methods, e.g., extreme toxicity to both animals and humans.

The phenolic glucoside fraction, as described by Hagin, et al., Ibid., was split into five fractions labeled 1-5, decreasing in molecular weight from ≧4159 for fraction 1 to 150 for fraction 5. It was found that the glycosides were composed solely of glucose and a number of aglycons. As previously reported, (Hagin, et al., supra) allelopathic activity toward the seedlings of a number of plant species existed in fractions 4 and 5. The principal aglycons in fractions 4 and 5 were identified as 5-Hydroxy Indole Acetic Acid (5-HIAA), 5-Hydroxy Tryptophan (5-HTP) and Tryptophan (TP). Smaller amounts of these aglycons existed in fractions 1-3. The principal allelopathic aglycons in quackgrass, toward a number of plant seedlings, proved to be 5-HIAA and 5-HTP.

Unexpectedly, fraction 3 showed significant toxicity towards *Deroceras reticulatum* and *Deroceras laeve* with smaller effects in fractions 1 and 2, indicating the presence of additional compounds other then 5-HIAA, 5-HTP and TP exhibiting anti-slug activity. Fractions 4 and 5 had no effect on the two slug species indicating that these three aglycons had little effect on slugs.

Compounds identified tested to have anti-slug activity are formulated into a bait pellet composition comprising: a)

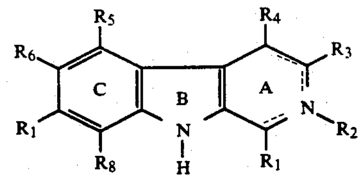

where $R^1$=H or OH $R_2$=H or COOH $R_3$=H or COOH $R_4$=H or halogen $R_5$=H, halogen or OH $R_6$=OH, H or halogen $R_7$=OH, H or halogen $R_8$=OH, H or halogen and wherein ⋯ represents a single or double bond, and further where no two double bonds are adjacent, and that the number of substituents attached to any atom possessing a double bond be limited to comform with valence requirements, and b) an effective amount of a slug bait sufficient to attract slugs.

The bait pellet is administered to a predetermined area. Slugs are lured to the area to feed on the poisoned bait pellet composition and die. Use of these pellets are effective in the management of slug pests.

DETAILED DESCRIPTION OF THE INVENTION

EXAMPLE 1

Reagents and Standards. All reagents, solvents and standards were analytical grade. The following standards and reagents were purchased from Sigma Chemical Company: 5-hydroxyindoleacetic acid, (5-HIAA), 98–100%; L-tryptophan, Sigma grade; 5-hydroxy-L-tryptophan (5-HTP), 99%.

Synthesis of 1,2,3,4,-tetrahydro-β-carboline-3-COOH (TβC-3-COOH) was accomplished by the method of Brossi, et al., J. Med. Chem., vol. 16, no. 4, (1973), pp. 418–420. Reaction between L-TP and formaldehyde by Pictet-Spengler condensation produced the final product in 40% yield. Synthesis of 6-hydroxy-1,2,3,4-tetrahydro-β-carboline-3-COOH (6HTβC-3-COOH) was accomplished by condensation between 5-HTP and formaldehyde (Brossi, et al., Ibid.). The pure product was isolated with a yield of 81%. All solvent operations, derivatizations and reactions were carried out in a fume hood.

Materials. Quackgrass roots and rhizomes (collectively called roots) were harvested from an established quackgrass sod in Tompkins County, New York. The plants had just completed pollination at the time of harvest. Roots were washed several times with tap water, rinsed with distilled water and blotted dry with absorbent paper. The roots were oven dried at 60°–70° C., ground in a Wiley mill to pass through a 40 mesh screen and stored in glass bottles in a freezer at −20° C. until extraction.

Animal Test Species. The slug species *Deroceras reticulatum* (Muller) and *Deroceras laeve* (Muller), used in laboratory tests, were harvested using trapping methods as outlined by Rollo, et al., Proc. Entom. Soc. Ont., vol. 105, (1974), pp. 89–95, incorporated herein by reference. Slugs were kept in polycarbonate animal cages 35 cm L×30 cm W×16 cm H. The bottom and sides were lined with paper towels moistened with distilled $H_2O$ and the top was covered with a glass plate to retain the slugs. A maximum of 40 slugs per cage was maintained to prevent cannibalism. Slugs were fed a pelleted food placed on a glass plate in the bottom of the cage. They were kept in an incubator set at 20° C. in the dark prior to testing of the bait pellet. The food source was removed 24 hours prior to testing of the bait pellet. The slug species *Arion subfuscus* (Draparnaud) was the principal slug found in the field test. Slugs were identified according to Chichester, et al., Malacol. Int. J. Malacol., vol. 7, nos. 2–3, (1969), pp. 313–346, incorporated herein by reference.

Three fresh water snail species were tested; *Helisoma trivolvis* (Say), *Lymnaea Humulus* (Say) and *Physa gyrina* (Say). The first two were harvested from a pond and stream near Ithaca, N.Y. in early spring. *Physa gyrina* was purchased from Wards Natural Science Establishment, Inc., 5100 West Henrietta Rd., Rochester, N.Y. Identifications were confirmed according to Harman, et al., Agriculture, vol. 1, (1971), pp. 1–68, incorporated herein by reference.

Snails were tested for sensitivity to quackgrass isolates (after acclimatization for 24 hours in 1 liter beakers of distilled $H_2O$) in a growth chamber maintained at 20° C. with a 14 hour day length.

The pink soil worm *Eisenia rosea* (Savigny) was harvested in late fall from a local garden. Identification was confirmed using the key of Reynolds, "The Earthworms (Lumbricidae and Sparganophilidae) of Ontario," Life Sci. Misc. Pub., R. Ont. Mus., 1977, pp. 78–83, incorporated herein by reference.

This earthworm was tested directly on transfer to the lab.

EXAMPLE 2

Purification and Chemical Analysis

Sample Extraction and Purification. Plant material was extracted by a two stage aqueous alcohol system employing methanol or isopropanol as the organic phase. The extract was taken to dryness using a rotary vacuum evaporator. The dried residue (total extract) was taken up in distilled water and subjected to successive hexane and ether extractions in a separatory funnel to produce two fractions labeled "lipids" and "organic acids," respectively. The remaining water solution was adjusted to pH 7.5 and passed through a glass column containing Amberlite XAD-2 resin. The material passing through the column along with a distilled water rinse was concentrated on a rotary vacuum evaporator. This fraction was labeled "water soluble." Material retained on the XAD-2 column was eluted with 70% methanol /30% $H_2O$, v/v. The eluate was concentrated to dryness on a rotary vacuum evaporator. This fraction was labeled "phenolic glycosides."

Phenolic glycosides were fractionated by molecular size by passing a concentrated water solution of the glycosides through a glass column packed with Sephadex G-25. The column was eluted with distilled water to produce five column fractions, labeled 1–5, based on visible color or UV absorption.

Carbohydrate Determinations. Initially, samples of phenolic glycosides (200 mg) were mixed with 20 ml of 7% HCl in water, w/v, sealed in teflon capped pyrex reaction vessels and heated at 100° C. for one hour (hr). The cooled hydrolysis mixture was extracted three times with 1-butanol which removed the released aglycones. The remaining aqueous solution was neutralized to pH 7.0 with 5% $NaHCO_3$. Traces of 1-butanol were removed by evaporation. The remaining aqueous solution was analyzed for sugar content by gas chromatography, using the method of Sweeley et al., J. Am. Chem. Soc., vol. 85, (1963), pp. 2497–2507.

Stereo-configuration of the glucosides was determined by subjecting 1 g samples of the phenolic glucosides to hydrolysis by either α or β-glucosidase using methods of Sumner, et al., Chemistry and Methods of Enzymes, Academic Press, New York, 1953, pp. 106–110, and employing a continuous liquid/liquid extractor with 1-butanol as the extractant for released aglycones. The hydrolysis was conducted for 72 hours. The hydrolytic system was tested with p-nitrophenyl-β-D-glucopyranoside prior to attempting to hydrolyze quackgrass phenolic glucosides. β-glucosidase released p-nitrophenol while α-glucosidase did not.

Aglycon Isolation from Phenolic Glucosides. Phenolic glucosides isolated from dried plant material proved to be extremely complex although they appeared to be based on aglycons absorbing UV light at a maximum at 278–280 nm. Further, isolated aglycons proved to be unstable, converting to a number of other compounds either in water or alcohol solvents. A hydrolytic method was devised which worked well with phenolic glucosides isolated from fresh plant material. One gram of isolated phenolic glucoside was mixed with 50 ml of 0.1N HCl, placed in a 50 ml sample bottle, flushed with $N_2$ and sealed with a teflon cap. The bottle was stored in a refrigerator set at 5° C. for 72 hours. It was shaken at least three times in this period. After 72 hours the hydrolysate was extracted three times with 1-butanol. The combined 1-butanol fractions were extracted in a separatory funnel with distilled water to remove excess HCl. Isolated aglycones were either used directly or the 1-butanol (after drying over $MgSO_4$) was removed on the rotary vacuum evaporator and the remaining aglycones stored in the dry state.

Fractionation of Phenolic Glucosides by Molecular Size. Phenolic glucosides were split into five column fractions on a 45 mm dia.×55 cm high glass column packed with Sephadex G-25, medium size. The sample was dissolved in a small volume of distilled water, applied to the column and eluted with distilled water. Fractions were made, based on visible color or UV absorption intensity at 280 nm. All fractions eluted in about 5 column void volumes. Fraction 1 included material beyond the exclusion limit of Sephadex G-25 (>5,000 MW). fractions 4 and 5 included monoglucosides of cinnamic acids (~310 MW). All fractions showed allelopathic activity towards alfalfa seedlings but activity was concentrated in fractions 4 and 5.

Fractionation of Dried Quackgrass Root Phenolic Glucoside Aglycons by Molecular Size. The hydrolytic method employed in carbohydrate determinations was used to provide a free, dry aglycon fraction from the total phenolic glucoside isolate. The isolated aglycons were dissolved in 50/50, v/v, methanol/$H_2O$ and applied to a XAD-2 column. The column was then flushed with 5 column void volumes of $H_2O$ to remove traces of salts and sugars. The adsorbed aglycons were removed from the column with 70% methanol/30% $H_2O$, v/v, and concentrated to dryness. Aglycons were fractionated on a 25 mm dia.×100 cm high glass column packed with Sephadex LH-20. Aglycons were dissolved in a small volume of methanol and eluted with methanol. Fractions were separated on the basis of visible color or UV absorption at 280 nm. Seven fractions were produced in about 5 column void volumes. Fraction 1 occupied the first column void volume. It still displayed UV absorption at 278–279 nm indicating that hydrolysis of the total phenolic glucoside isolate had been incomplete. Fractions 1–5 showed allelopathic activity toward alfalfa seedlings with activity concentrated in fractions 4 and 5. Fractions 6 and 7 showed no measurable allelopathic activity. Colored material gradually built up on both Sephadex columns and they were periodically cleaned with 0.1N HCl followed by a distilled water rinse. There was no measurable allelopathic activity in the cleanup fractions.

TLC and HPLC of Aglycons. The most useful TLC system for quackgrass phenolic aglycons employed silica gel G plates (0.25 mm thick layer) and a solvent mixture of n-butanol/acetic acid/$H_2O$. 4/1/1, by volume. Visualization reagents were prepared and used as found in the *Handbook of Chromatography*, (1972). Sulfuric acid and charring was used for general visualization. Ferric chloride-ferricyanide reagent was used to visualize phenolic compounds. Modified Ehrlich reagent (p-dimethylaminocinnamaldehyde) was used to visualize primary amines. The specific reagent, nitrosonaphthol-nitrous acid was used to visualize 5-hydroxyindoles. Long wave (360 nm) UV light was used to expose fluorescent compounds. TLC systems and listed $R_F$ values listed by Jepson, J. B., Chromatographic and Electrophoretic Techniques, 3rd ed., Smith, I., Ed., John Wiley & Sons, New York, 1969, vol. 1. ch. 9, for indoles and related compounds were used for confirmation of identities of 5-HIAA and 5-HTP.

HPLC was conducted using a Micromeretics Model 7000 High Pressure Liquid Chromatograph. A stainless steel column, 4.6 mm ID×25 cm long packed with 5 μm Spherisorb ODS (obtained from Sulpelco) was used for separations. The solvent system employed was 70% pH 7.5 phosphate buffer (containing 0.01M tetrabutylammonium hydroxide as an ion pair reagent), 30% methanol. The flow rate was set at 0.15 ml/min., and temperature at 20° C. The detector employed was fixed UV emitting at 280 nm. Under these conditions 5-HIAA eluted at ~23, 5-HTP ~25, TP ~29, and IAA at ~33 minutes, respectively. Column retention times increased over a matter of months. Quantitation of the above listed compounds was achieved by measurement of recorded peak areas and comparison to standard curves of known standards. Under the conditions of analysis employed, IAA could be detected at 0.01 ppm relative to dry weight of plant material.

UV, IR, Mass Spectral, C,H,N,O, and Elemental Analysis. UV/VIS spectrophotometry was performed using a double beam spectrophotometer (Beckman Model DB). It was operated in the spectral range of 220–700 nm, utilizing one cm quartz cells maintained at 20° C.

IR spectrophotometry was performed with a double beam infrared spectrophotometer (Perkin Elmer Model 783) operating in the frequency range of 4000–200 $cm^{-1}$. KBr pellets were used to contain samples.

CHN analysis were performed utilizing a carbon, hydrogen, nitrogen analyzer (Hewlett Packard, Model 185). Oxygen was determined by difference since other elements were not present. 0.7 mg samples were used in the analysis.

Qualitative elemental analysis was performed according to methods of Pasto, et al., Organic Structure Determination, Prentice-Hall, Englewood Cliffs, NJ, 1969, pp. 315–321.

Mass spectral analysis was performed at the Mass Spectrometer Facility, Chemistry Dept., Cornell University, Ithaca, N.Y. 14853-0144. Isolated aglycons and phenolic glucosides as well as standards were subjected to both EI and CI mass spectrometry. Chemical ionization mass spectrometry employed methane as the reagent gas. Spectra were recorded as the samples were heated from ambient to 500° C. The presence and identification of cinnamic acid derivatives in phenolic aglycone fractions was determined by EI GC-MS of TMS derivatives. A 3% OV 101 liquid phase was employed and temperature programmed from 125° to 250° C. Peak identification was accomplished using a PBM and STIRS Version 4.0 computerized mass spectral identification program. Mass spectral data was interpreted as required.

Chemical ionization mass spectrometry of fraction 3 indicated a principal mass peak (50% of base peak produced at a probe temperature of 460° C.) at m/z 232. A secondary peak was produced as the probe was heated through 300°-400° C. at m/z 233. Assuming that these fragments represented M+1 peaks, it was deduced that the compound had a mass of 232 and amu 231 was a M−1 peak. The M−1 peak was presumed to have been produced from the aglycone split from glucose. 5-HTP possesses amu 220 and a formula of $C_{11}H_{12}N_2O_3$. The calculated formula of amu 232 is $C_{12}H_{12}O_3$. the compound was tentatively identified as 6-HTβC-3-COOH. This compound is known to be produced from 5-HTP in mammalian tissues along with TβC-3-COOH produced from TP. Both compounds were synthesized according to the methods of Brossi et al., supra and 6-HTβC-3-COOH proved to be identical to the principal material isolated from aglycones from fraction 3 (comparison by TLC, UV and IR methods).

TLC of Standards and Isolated Aglycones. The TLC system used primarily employed silica gel G plates (0.25 mm thick layer) and a solvent mixture of n-butanol/acetic acid/$H_2O$, 4/1/1, by volume. Under this system 5-HTP, TβC-3-COOH and 6-HTβC-3-COOH had $R_F\times 100$ values of 51, 56 and 27 respectively.

EXAMPLE 3

Food and Bait Formulations

Slug Food and Bait. Original food testing methods used by Hagin, et al., Abstract of Papers, National Meeting of the Weed Science Society of America, Sheraton Inn, Seattle, WA, Feb. 5-7, 1985, Abstract 170, relied on an artificial medium developed by Wehlan, R.J., J. Appl. Ecol., vol. 19, (1982), pp. 89-94, incorporated herein by reference. In short, this method used calcium alginate gel disks to provide a control food based on a lettuce leaf extract. It is envisioned that other plant sources or pure chemicals could replace the lettuce as functional equivalents for purposes of testing. Lettuce extract controls, in our hands, had too many problems with mold growth and the control food was altered to have red clover as its base (*Trifolium repens L.*). This proved to be more palatable to slugs than lettuce based alginate gels and had fewer problems with molds.

To overcome the necessity to continually make gels for feeding slugs, a pelleted food was made up using powdered red clover, powdered bran, powdered wheat germ and dried milk in proportions of 2:1:1:1:. This served as the regular laboratory food for slugs. For chemical tests the appropriate level of chemical was added in solution, the material was blended and additional water was added, as needed, to form a thick paste. The paste was forced through 4 mm round holes in a food grinder to form pellets. The pellets were baked at 60° C. and stored in plastic bottles prior to use.

Bait for the field test of 6-HTβC-3-COOH was made up of ingredients in the following proportions: 250 g of dry corn bran, 20 g dry powdered milk and 20 g of amylose. This was blended with a food mixer. While blending, 400 ml of Matts brand draft beer containing 350 mg of 6-HTβC-3-COOH was added. Additional beer was added as needed to make a thick paste. Pellets were formed and dried as noted above. The level of chemical in the bait was set at 1000 ppm on a dry weight basis.

EXAMPLE 4

Test Methods

Forced Contact Methods. For forced contact of chemicals with either slugs or earthworms, single animals were placed inside 35×80 mm OD soxlet extraction thimbles. The open end was folded over and stapled shut. The sealed tubes were placed in individual compartments of 12 section plastic boxes. Each section was 4.5 cm W×8 L×4 cm H. Four ml of distilled water (control) or 4 ml of 1000 ppm test solution was applied to the thimbles. The boxes were closed and the test animals were kept in a dark incubator set at 20° C. for 24 hours. Surviving animals were transferred from the sealed thimbles to a second plastic box (each section of which was lined with water moistened filter paper), a lettuce leaf was added and the closed boxes were placed in the incubator. Observations were made for up to four days. Ten animals were used per treatment and the treatments were replicated four times.

Snail Test Methods. Chemicals were tested on snails using standardized methods [Webbe, et al., Ann. Trop. Med. Parasitol., vol. 58, (1964), pp. 234-239 and Malek, et al., Medical and Economic Malacology, Academic Press, Inc., New York, 1974, 398 p.]. Each species was exposed to a distilled water control, 5, 50, or 500 ppm of phenolic glycosides for 24 hours. Ten animals were used for each treatment level. After 24 hours the animals were washed with distilled water and transferred to distilled water for observation. Pieces of seaweed were added to the beakers as a food source and the snails were observed for up to four days.

Laboratory Slug Test Methods Employing Treated Food. Two 9 cm diameter, Whatman No. 1 filter papers were placed in the bottom of a 9 cm diameter petri dish and moistened with water. A 12 mm in length control or chemical test pellet was placed on a 18 mm diameter cover slip and moistened with distilled water. Twelve mm pellets averaged 92 mg dry weight each. After weighing, the pellet and cover slip was placed in the center of the filter paper. One slug of the test species was placed in the petri dish, the cover was placed on and the petri dish was placed in a dark incubator set at 20° C. Ten animals were used for each control or chemical treatment. Food consumption and activity was recorded daily and observations were made for 7 days. Tests in which more than two of the control slugs died were discarded on the basis that the population was unhealthy. Feeding tests were conducted in this fashion up through Feeding Trial I. For Feeding Trial II, chemicals in water solution were applied to fresh control pellets 12 mm long. 5-HIAA was added at a level of 50 μg/pellet. Other chemicals were added at a level of 12.5 μg/pellet. Moistened pellets and cover slips were weighed as noted earlier. At the end of the test evaluation period all slugs either dead or inactive were considered to be dead (Malek, et al., Ibid.).

EXAMPLE 5

Feeding Trials

Feeding Trials I and II. Feeding Trials I and II were designed to test the molluscicidal effectiveness of 5-HIAA, TβC-3-COOH and 6-HTβC-3-COOH and a combination of 5-HIAA with each of the latter two. Concentrations used were noted above. Feeding Trial II was designed to test the possibility of compound alteration or breakdown during drying of pellets. Slugs averaged 0.2 g each in feeding trials I and II.

The two compounds synthesized from EXAMPLE 2 along with 5-HIAA were tested in two feeding trials against the slugs *Deroceras reticulatum* and *Deroceras laeve*. The results of the test against *Deroceras reticula-*

*tum* were discarded due to general poor health of the test animals. The tests on *Deroceras laeve*, a smaller species of slug than *Deroceras reticulatum* with greater resistance to molluscicides (Godan, Pest Slugs and Snails, Springer-Verlag, New York, 445 p., Chapter 3, p. 189) are shown in Tables I and II.

In both trials 6-HTβC-3-COOH proved to be the most effective molluscicidal compound while TβC-30-COOH showed variable activity. When in combination, 5-HIAA appeared to exhibit some antagonistic activity toward 6-HTβC-3-COOH. Extrapolating backwards from the 100% kill for 6-HTβC-3-COOH in Table I and the 80% kill for the same compound in Table II it was estimated that the $LD_{50}$ for slugs relative to the compound approximated 5 mg/kg of slugs.

TABLE 1

Feeding Trial 1: Compounds potentially molluscicidal to the slug *Deroceras laeve*.

| compound[a] | mg bait consumed | slugs dead | μg chemical/ slug | μg chemical/ g slugs |
|---|---|---|---|---|
| control | 36 ± 20 | 1 | 0 | 0 |
| 5-HIAA | 28 ± 17 | 10 | 28 | 140 |
| 6-HTβC-3-COOH | 20 ± 16 | 10 | 5 | 25 |
| TβC-3-COOH | 25 ± 20 | 0 | 6.2 | 31 |
| 5-HIAA + | 10 ± 6 | 9 | 10 | 100 |
| 6-HTβC-3-COOH | | | 2.5 | 12 |
| 5-HIAA + | 31 ± 33 | 2 | 31 | 156 |
| TβC-3-COOH | | | 7.7 | 38 |

[a]5-HIAA was supplied at 1000 ppm and the other compounds were supplied at 250 ppm (dry weight basis).

TABLE II

Feeding Trial 2: Compounds potentially molluscicidal to the slug *Deroceras laeve*.

| compound[a] | mg bait consumed/ slug | slugs dead | μg chemical/ slug | μg chemical/ g slugs |
|---|---|---|---|---|
| control | 70 ± 33 | 2 | 0 | 0 |
| 5-HIAA | 29 ± 35 | 1 | 16 | 80 |
| 6-HTβC-3-COOH | 10 ± 4 | 8 | 1.4 | 7 |
| TβC-3-COOH | 35 ± 31 | 7 | 4.9 | 24 |
| 5-HIAA + | 34 ± 35 | 6 | 18 | 90 |
| -HTβC-3-COOH | | | 4.8 | 24 |
| 5-HIAA + | 32 ± 23 | 4 | 17 | 85 |
| TβC-3-COOH | | | 4.5 | 22 |

[a]Chemicals were applied to fresh control bait pellets in solution. 5-HIAA was added at a level of 50 μg/pellet. Other chemicals were added at a level of 12.5 μg/pellet.

On this basis 6-HTβC-3-COOH would be rated as a highly toxic compound toward slugs (Osweiler, et al., Clinical and Diagnostic Veterinary Toxicology, Kendal/Hunt, Dubugue, Iowa, 3rd ed., 1985, pp. 3–8.

Brossi, et al., supra, concluded that this compound exhibits little mammalian toxicity. Based on this information and the lack of activity toward earthworms or snails when tested against the quackgrass phenolic gylcosides it was concluded that 6HT C-3-COOH is likely to be highly specific toward slugs, with little toxicity toward other species, particularly mammals.

Feeding Trial I utilized chemicals added before baking and feeding Trial II utilized chemicals added after baking. Comparing the results of Table I and Table II relative to the method of adding chemicals before or after baking the bait; two conclusions can be drawn. First, baking may alter 5-HIAA in some way to make it more toxic to slugs. Secondly, 6-HTβC-3-COOH loses some activity due to the baking process. From these conclusions it appears that a method should be found to add 6-HTβC-3-COOH to the food mixture and pellets formed (in some way) without heat. Alternatively, the compound can be added uniformly to pre-baked pellets in order to retain anti-slug activity.

Buckholtz, N. S., Life Sci., vol. 27, (1980), pp. 893–903, indicated that TetraHydro-β-carboline compounds act as nerve poisons in mammalian systems and may specifically act by inhibiting monoamine oxidases in the liver. Homeida, et al., J. Vet. Pharmacol. Therap., vol. 5, (1982), pp. 77–81, found metaldehyde to act in a similar manner in mice. Singh, et al., Toxicol. Let., vol. 21, (1984), pp. 309–314 found the latex of *Euphorbia Royleana* to act as a nerve poison in the snail *Lymnaea Acuminata* by altering biogenic amine levels. In this study three species of slugs were killed by 6-HTβC-3-COOH while three species of freshwater snails were unaffected by it. These results indicate that slugs and snails either possess different specificity or different detoxification mechanisms for the compound. It is envisioned that the compound, 6-HTβC-3-COOH, can be used to elucidate species differences for the production of other species-specific molluscicicdes.

EXAMPLE 6

Field Tests

Molluscicidal Field Test. An experimental site was established in Lansing, N.Y., adjacent and parallel in the long dimension (north-south), to a field of crownvetch (*Coronilla varia*L. ). The site was located at the northwest corner of the crownvetch field—both the experimental area and the field bordered on the north by a highway. The south and west sides of the site were bordered by bluegrass sod. The land was conventionally tilled and laid out in 12 north-south rows 0.75 m wide. The two east rows were planted to sweetcorn (*Zea mays* L., var. Pennfresh ADX). The next two rows to the west were planted to snapbeans (*Phaseolus vulgaris* L., var. Long Tendergreen). A variety of vegetables were planted in the remaining eight rows to the west.

In mid-June rains (as periodic light showers), came as a near daily occurrence. Temperatures reached daily highs of up to 30° C. and lows around 20° C. The humidity averaged near 100%. Conditions were ideal for slug growth and reproduction (Godan, D., Pest Slugs and Snails, Springer-Verlag, New York, 1983, 445 p.). Rainfall (in cm) for the period was as follows: 6/21, 0.5; 6/22, 0.5; 6/23, 3.8; 6/25–6/29, 1.9; 6/30, 0.5; 7/1, 0.25; 7/2, 0.25 and 7/3, 1.27.

On the evening of 6/25 a large population of the slug *Arion subfuscus* moved from the crownvetch field, passing through the two corn rows, and heavily attacked the beans. Some sections of the bean plants, which should have been 10–15 cm tall, were completely defoliated. An area enclosing the corn and bean rows, 3.9 m wide×23 m long was marked out and 250 g of molluscicide bait (containing 1000 ppm of 6-HTβC-3-COOH) was uniformly spread around the perimeter. The bait was spread in a band 38 cm wide centering outside the bean rows on the west and outside the corn rows on the east. The bait crossed the bean and corn rows on the north and south. The bait was applied at 8:00 PM initially. As the bait was exhausted it was replaced at 125 g/treatment around the perimeter. It was reapplied 7/1, 7/3 and 7/5.

Four randomized sections, 38 cm×91 cm were marked out between the corn rows and the crownvetch as well as within the bean rows. Slugs were counted before the experiment began and periodically during it.

Pictures were taken initially as well as periodically through bean harvest.

The results of the molluscicide field test are listed in Table III.

TABLE III

| | | Slug numbers/meter$^2$ of treated perimeter rows or enclosed bean rows. | | | |
|---|---|---|---|---|---|
| date: | time: | east side[a] | bean rows | west side | presence of bait |
| 6/25[b] | 7:45 PM | 29 ± 9 | 78 ± 34 | 0 | − |
| | 8:00 PM | Bait Applied | | | + |
| | 8:15 PM | 26 ± 8 | 1 ± 3 | 0 | + |
| | 8:30 PM | 32 ± 6 | 0 | 0 | + |
| 6/29 | 10:00 AM | 1 ± 1 | 1 ± 1 | 1 | + |
| 6/30 | 11:00 AM | 1 ± 1 | 0 | 1 | + |
| 7/1[c] | 8:00 AM | 0 | 17 ± 14 | 0 | − |
| | 8:15 AM | Bait Applied | | | + |
| 7/2 | 9:00 AM | 12 ± 14 | 1 ± 1 | 11 | − |
| 7/3 | 9:00 AM | 19 ± 6 | 26 ± 12 | 14 | − |
| | 9:30 AM | Bait Applied | | | + |
| | 10:00 AM | 55 ± 14 | 9 ± 6 | 319 | + |
| 7/4 | 9:00 AM | 0 | 1 ± 1 | 2 | + |
| 7/5 | 11:00 AM | 1 ± 3 | 0 | 0 | − |
| | 11:30 AM | Bait Applied | | | + |
| | 12:00 PM | 12 ± 9 | 0 | 12 | + |
| 7/6 | 8:30 AM | 1 ± 1 | 0 | 8 | − |

[a]Means ± standard deviation for 4 replicates; entire west side was counted and adjusted to match count areas for east side and bean rows.
[b]Mature slugs, average weight 0.8 g each.
[c]Immature slugs that were approximately one half the size of mature slugs.

*Arion subfuscus* is a robust slug primarily inhabiting woodlands. Beyer, et al., Am. Midl. Nat., vol. 100, (1978), pp. 359-367, discussed the ecology and feeding habits as well as the distribution of this slug particularly in the Ithaca, N.Y. area. Chichester, et al., supra, noted that this slug has the potential to become the most serious slug pest in North America. It was therefore noteworthy that the formulated bait controlled this slug under intense feeding pressure. In Table II we note that two waves of slugs from the crownvetch field attacked the plants in the experimental area. The first wave of adult slugs, occurring at the beginning of the experiment 6/25, was essentially eliminated by the bait treatment by 6/30. At this time, the original bait was gone. Three additions of bait were applied 7/1, 7/3 and 7/5. The second wave of slugs began arriving on 7/1 and was controlled in the experimental area by 7/5. Further applications of molluscicide were unnecessary and the bean crop proceeded to maturity and produced a normal crop in areas which had not originally been defoliated.

The development of an effective and attractive bait was almost as important as the identification and testing of the molluscicide itself. Unexpectedly, the treated bait was so attractive that within 30 minutes after application of the first bait all of the slugs in the bean rows left the beans and began devouring the bait. This occurred for as long as the bait was available—over a week after the last application. The treated bait therefore has considerable toxicity for a resonably long time under conditions of high humidity.

Godan, supra, discussed the problems related to the control of pest gastropods. In addition to problems associated with finding additional effective and specific molluscicides she stated: "It is clear that the problem of finding a substance as carrier base of the molluscicide and which is really attractive to most, if not all the gastropods in an infested area has not been solved." (Godan, supra). The bait formulated as a molluscicide carrier in this study as provided in the disclosure effectively addresses the problem as she stated it.

In accordance with the specific embodiments of the present invention there has been provided compositions and methods for the control and erradication of slug pests. It can be seen that many alternatives and variations can be practiced from the benefit of this disclosure. The spirit and scope of the instant invention is intended to encompass all such variations and alternatives.

We claim:

1. A pesticide composition for the erradication of slug pests comprising:

a) an effective amount of a slug bait, sufficient to lure slugs and induce said slugs to feed, and b) a molluscicidally effective amount of a compound of the formula:

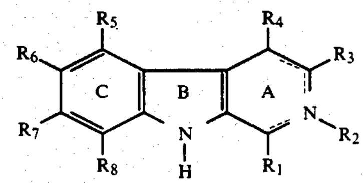

where $R_1$=H or OH
$R_2$=H or COOH
$R_3$=H or COOH
$R_4$=H or halogen
$R_5$=H, halogen or OH
$R_6$=H, halogen or OH
$R_7$=H, halogen or OH
$R_8$=H, halogen or OH and wherein ⋯ represents a single or double bond, and further wherein no two double bonds are adjacent, and that the number of substituents attached to any atom possessing a double bond be limited to conform with valence requirements.

2. The pesticide composition of claim 1, wherein the compound is 6-hydroxy-1,2,3,4-tetrahydro-β-carboline-3-carboxylic acid.

3. A method for the control and erradication of slug pests comprising:

a) applying to a predetermined agricultural site a pesticide composition comprising a molluscicidally effective amount of a compound of the formula:

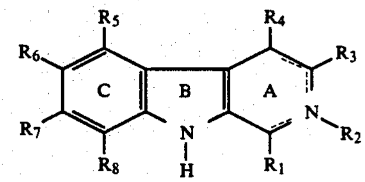

where $R_1$=H or OH
$R_2$=H or COOH
$R_3$=H or COOH
$R_4$=H or halogen
$R_5$=H, halogen or OH
$R_6$=H, halogen or OH
$R_7$=H, halogen or OH
$R_8$=H, halogen or OH and wherein ⋯ represents a single or double bond, and further wherein no two double bonds are adjacent, and that the number of substituents attached to any atom possessing a double bond be limited to conform with valence requirements.

4. The method of claim 3, wherein the compound is 6-hydroxy-1,2,3,4-tetrahydro-β-carboline-3-carboxylic acid.

5. The method of claim 3 which additionally comprises:

a) an effective amount of a slug bait, sufficient to lure slugs and induce slugs to feed.

6. The method of claim 4 which additionally comprises:

a) an effective amount of slug bait, sufficient to lure slugs and induce said slugs to feed.

* * * * *